United States Patent

Gunn et al.

[11] Patent Number: 5,133,932
[45] Date of Patent: Jul. 28, 1992

[54] BLOOD PROCESSING APPARATUS

[75] Inventors: Andrew Gunn, Angus; Ian D. Cameron, Dundee, both of Scotland

[73] Assignee: Iatros Limited, Scotland

[21] Appl. No.: 576,481

[22] PCT Filed: Mar. 28, 1989

[86] PCT No.: PCT/GB89/00318

§ 371 Date: Sep. 26, 1990

§ 102(e) Date: Sep. 26, 1990

[87] PCT Pub. No.: WO89/09067

PCT Pub. Date: Oct. 5, 1989

[30] Foreign Application Priority Data

Mar. 29, 1988 [GB] United Kingdom ............ 8807380

[51] Int. Cl.$^5$ ............................................. A61L 2/10
[52] U.S. Cl. ............................... 422/24; 250/435; 250/455.11; 210/748; 210/243
[58] Field of Search ............ 422/24, 120; 250/435, 250/455.1; 426/248; 435/284, 285; 210/748, 243

[56] References Cited

U.S. PATENT DOCUMENTS

| Re. 24,822 | 5/1960 | Pallotta et al. | 435/285 |
| 2,001,555 | 5/1935 | Trebler | 250/434 |
| 3,814,680 | 6/1974 | Wood | 210/748 |
| 3,894,236 | 7/1975 | Hazelrigg | 250/435 |
| 3,926,556 | 12/1975 | Boucher | 422/21 |
| 3,994,686 | 11/1976 | Rauser et al. | 426/248 |
| 4,438,337 | 3/1984 | Forrat | 210/243 |
| 4,798,702 | 1/1989 | Tucker | 422/24 |
| 4,948,980 | 8/1990 | Wedekamp | 250/435 |

FOREIGN PATENT DOCUMENTS

| 138489 | 9/1984 | European Pat. Off. |
| 240152 | 2/1987 | European Pat. Off. |
| 8701221 | 1/1987 | Fed. Rep. of Germany |
| WO86/04505 | 10/1985 | PCT Int'l Appl. |
| WO88/01510 | 8/1987 | PCT Int'l Appl. |
| 321639 | 8/1928 | United Kingdom |
| 574803 | 1/1943 | United Kingdom |
| 639467 | 3/1947 | United Kingdom |
| 1224198 | 12/1967 | United Kingdom |

OTHER PUBLICATIONS

Gerald A. LoGrippo, "Antigenicity of Combined β--Propiolactone and Ultraviolet Inactivated Virus Vaccines", *J of Immunology*, vol. 75:128, 1958.
Gunn et al Immunology 50 477 (1983).

*Primary Examiner*—Robert J. Warden
*Assistant Examiner*—Laura E. Collins
*Attorney, Agent, or Firm*—Krass & Young

[57] ABSTRACT

The present invention relates to the sterilization (in the sense of rendering free from cells or organisms capable of division e.g. lymphocytes, protozoans, bacteria, viruses) of blood or other fluids. The present invention provides an apparatus (1) for use in the ultraviolet irradiation of the fluid (8), which comprises a vessel (2) having side walls (4) substantially transparent to ultraviolet radiation of an effective inactivating wavelength; a turning vessel support (3) for supporting and allowing said vessel to turn on said support which is driven (23) so as to directly or indirectly turn the vessel on the support. U.V. irradiation means are provided for irradiating at least part of the turning vessel (2). In use of the apparatus a thin layer (9) of the fluid (8) adjacent the wall surface (10) of the side wall (4) is carried round past the ultraviolet irradiation means (7) and sterilized thereby and mixed with the main body of said fluid (8). The present invention also provides a method of inactivating undesired microorganisms in a biological fluid (8) in an apparatus (1) of the invention.

11 Claims, 1 Drawing Sheet

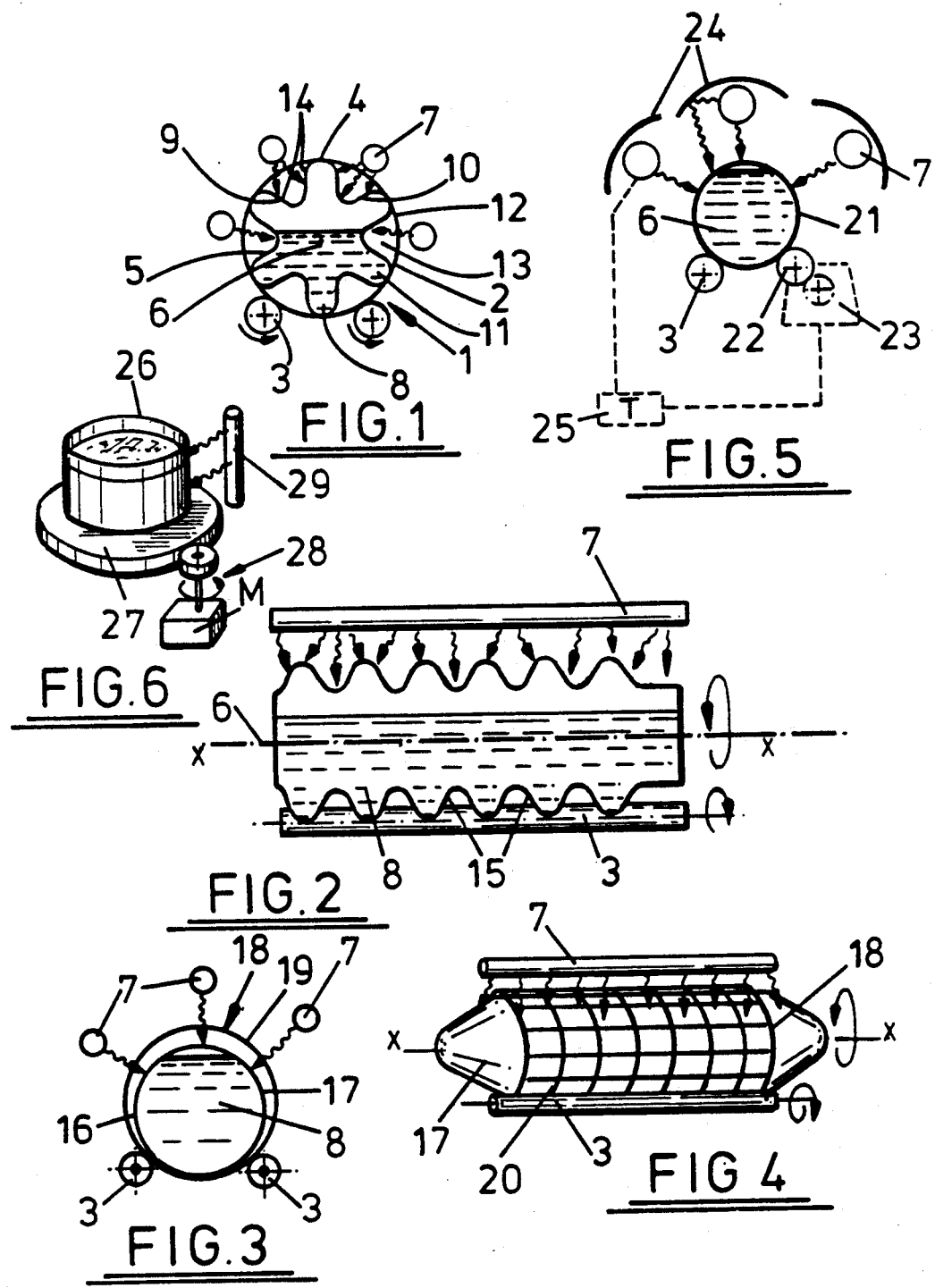

BLOOD PROCESSING APPARATUS

BACKGROUND OF THE INVENTION

The present invent-ion relates to the sterilisation (in the sense of rendering free from cells or organisms capable of division e.g. lymphocytes, protozoans, bacteria, viruses) of blood and blood products or other fluids i.e. fluids having a biological origin and/or for use in biological systems including for example nutrient and buffer solutions, plasma, anti-haemophillic globulin etc., and in particular to means suitable for use in such a procedure, enteral or parenteral or outwith the body e.g. laboratory reagents, tissue culture or microbiological systems etc.

Conventionally sterilisation of human blood products is generally effected by incubation thereof at a temperature of the order of 78° C. for an extended period of time of perhaps 48 to 72 hours. This procedure is however relatively time consuming and occupies subsantial amounts of relatively large scale apparatus and may result in substantial loss of potency.

It is an object of the present invention to avoid or minimize one or more of the above disadvantages.

SUMMARY OF THE INVENTION

The present invention provides an apparatus suitable for use in ultra-violet irradiation, said apparatus comprising an ultra-violet irradiation means formed and arranged to radiate ultra-violet radiation of an effective inactivating wavelength as defined herein, support means for supporting a substance to be irradiated in use of the apparatus and turning means formed and arranged to provide relative turning motion between said ultra-violet irradiation means and said substance, in use of the apparatus, said apparatus being characterised in that: said apparatus includes a vessel for containing a said substance in the form of a biological fluid in use of the apparatus, said vessel having side wall means substantially transparent to said ultra-violet radiation, a turning vessel support means formed and arranged for supporting said vessel and allowing said vessel to turn on said support means; a drive means formed and arranged for directly or indirectly turning said vessel on said support means; and said ultra-violet irradiation means being formed and arranged for irradiating at least part of a turning vessel on said support means, with ultra-violet radiation of an effective inactivating wavelength whereby in use of the apparatus a thin layer of said fluid adjacent the wall surface of said side wall means is carried round past the ultra-violet irradiation means and sterilised thereby and mixed with the main body of said fluid.

In a further aspect the present invention provides a method of inactivating undesired micro-organisms in a substance, said method comprising the steps of: providing relative turning motion between said substance and an ultra-violet irradiation means, characterised by the steps of: supporting a said vessel containing a said substance in the form of a biological fluid on said turning vessel support means; and operating said drive means for turning said vessel on said support means and said ultra-violet irradiation means for irradiating said fluid in said vessel for a period of time sufficient substantially to inactivate said undesired microorganisms therein.

Various forms of vessel turning may be used in accordance with the present invention. In general rolling of a generally tubular form of vessel is most preferred. Turning about various different axes is, however, also possible including, for example, rotation of a vessel about a generally vertical axis by supporting the vessel on a rotating turntable In this case in particular it will be appreciated that the turning speed is desirably selected so that it is sufficiently fast to provide a reasonable rate of mixing between the main body of the fluid and the thin layer adjacent to the outer side wall surface, and generally not so fast as to provide significant centrifugal separation of the fluid components and stratification thereof. Conveniently turning is effected at from 10 to 250 r.p.m.

It will be appreciated that the vessel may be only partly filled with the fluid undergoing irradiation or may be substantially filled so that at any given stage during irradiation the thin layer of fluid adjacent the wall surface of the side wall means may be simply in the form of an outer zone of an extended body of the fluid, or in the case of a partly filled rolling vessel, a discretely formed film the components of which are constantly being exchanged with the main body of fluid as rolling proceeds.

Any U.V. radiation known to be effective in inactivating microorganisms may be used in the apparatus and method of the invention. Suitable U.V. radiation sources include those producing radiation in the wavelength range from 100 to 400 nm preferably from 200 to 350 nm, for example UVA at approximately 320 to 400 nm, UVB at approximately 310 nm and UVC at approximately 254 nm.

Particular lamp sources which may be mentioned include those available from GTE Sylvania Ltd. of Charlestown, Shipley, West Yorkshire, Thorn EMI of Enfield, Middlesex and Philips Lighting of Croydon, Surrey, all in England.

The duration of irradiation required will depend on various factors such as the intensity, disposition, and number of sources used, the transmission characteristics of the vessel side wall material, the vessel configuration and hence the mixing efficiency therein and the surface area of the thin layer of fluid adjacent the vessel side wall, and the volume and nature of the fluid being treated. The required duration may however be readily determined by simple trial and error using suitable techniques known in the art for assessing inactivation of the relevant microorganisms and further details are provided hereinbelow. In general the duration will conveniently be in the range from 2 to 60 minutes, preferably from 5 to 30 minutes, e.g. 15 minutes, and the radiation sources are chosen and arranged, to provide an effective inactivating dosage of U.V. radiation within such a period.

It should also be noted that the present invention also includes within its scope indirect inactivation of microorganisms whereby a photoactivatable drug is incorporated in the fluid, said drug being converted from a non-inactivating form into a microorganism inactivating form by U.V. irradiation. One example of a photoactivatable drug of this type that may be mentioned is a psoralen e.g. 8-methoxy psoralen which upon exposure to U.V.-A radiation of 320 to 400 nm wavelength becomes capable of forming photoadducts with DNA in lymphocytes thereby inactivating these.

Various forms of vessel may be used in the apparatus and method of the invention including rigid or semi-rigid, generally structurally self-supporting—at least when filled with the fluid, bottles as well as generally flexible bags. In the latter case, especially when these are only partly filled there will generally be required a significantly higher degree of support during rolling. Such bags may however be more convenient due to their more or less collapsible nature which facilitates storage, packing and safety in transfusion.

In a further aspect the present invention provides a vessel for use in the apparatus and method of the invention which vessel comprises a generally tubular bag having side wall means substantially transparent to said ultra-violet radiation, and, advantageously, side wall support means formed and arranged for supporting said side wall means, at least during an ultra-violet irradiation phase, so that said vessel has a generally cylindrical form for rolling of the vessel during a said irradiation phase, whereby in use of the apparatus an extended thin layer of said fluid adjacent a side wall surface of said side wall means may be exposed to an effective sterilising dosage of ultra-violet irradiation and said thin layer is substantially mixed with the main body of fluid in the vessel as said vessel is rolled.

The side wall support means may be of any suitable form and may be formed integrally with the side wall means e.g. as corrugations formed in the side wall means which may for example, extend circumferentially, axially, or obliquely with respect to the central rotational axis of the vessel and which have the advantage of increasing mixing during rolling of the vessel. The side wall support means may also be in the form of a separately formed structure engagable with the side wall means so as substantially to support the bag when substantially filled with fluid, in a generally cylindrical form during rolling of the vessel. The side wall support means is conveniently formed and arranged so as to be detachably engagable with the bag side wall means to minimize the costs of individual biological fluid containers by enabling each support means to be used with a large number of bags.

Such detachable support means may have any suitable form and could for example be in the form of a generally tubular self-supporting structure of uv transparent material or a generally cylindrical cage of any convenient structural material, the radiation being allowed to pass between the spaced apart elements of the cage.

In a preferred aspect the present invention provides a vessel suitable for use in the ultra-violet irradiation of a biological fluid which vessel is generally cylindrical for rolling in use thereof during irradiation of a said fluid, and has corrugated side wall means substantially transparent to ultra-violet irradiation, whereby in use of the apparatus an extended thin layer of said fluid adjacent a side wall surface of said corrugated side wall means may be exposed to an effective sterilising dosage of ultra-violet irradiation and said thin layer is substantially mixed with the main body of fluid in the vessel as said vessel is rolled.

Thus with the present invention substantially complete and effective sterilisation of a biological fluid so as to inactivate one or more of bacteria, protozoa, including plasmodium the species responsible for malaria, trypanosomes, lymphocytes, and the like, by means of ultra-violet irradiation can be achieved quickly and economically without significant risk of impairing the functional properties of the fluid. Other microorganisms that may be inactivated to a greater or lesser degree include viruses, both DNA-type e.g. herpes simplex virus, and RNA type such as Human Immunodeficiency Virus, and pico-RNA viruses such as Coxsackie viruses.

The corrugated side wall means of the preferred embodiments may be of any suitable form. Thus the corrugations may extend transversely i.e. circumferentially, or longitudinally i.e. parallel to the central axis of rotation of the generally cylindrical vessel, or diagonally i.e. helically. Furthermore the corrugations may be rounded e.g. sinusoidal, or angular in their transverse cross-sectional shape. Also, especially where the vessel is of relatively flexible material such as thin silicone rubber, the corrugated wall means may be provided with support means such as ribs, rings, flanges, or the like extending across the corrugations so as to help maintain a said generally cylindrical shape at least during rolling of the vessel with said fluid therein about its central axis of rotation.

The abovementioned vessel side wall means may be made of various u.v.—transparent materials including for example silica and other u.v. - transparent glasses such as those available under the Trade Names Spectrosil and Vitreosil; silicones; cellulose products such as Cellophane (Trade Name); and plastics materials such as polytetrafluoethylene (PTFE), fluorinatedethenepropene (FEP), and preferably low density polyethylene (LDPE) or polyvinyl chloride (PVC).

BRIEF DESCRIPTION OF THE DRAWINGS

Further preferred features and advantages of the present invention will appear from the following detailed description given by way of example of some preferred embodiments illustrated with reference to the accompanying drawings in which:

FIG. 1 is a schematic transverse cross-section through a first apparatus of the invention with a first vessel embodiment;

FIG. 2 is a vertical longitudinal section through a similar apparatus with a second vessel embodiment;

FIG. 3 is a view corresponding to FIG. 1 of a further embodiment;

FIG. 4 is a perspective side view of another embodiment;

FIG. 5 is a transverse section through a still further embodiment; and

FIG. 6 is a perspective side view of yet another embodiment.

DETAILED DESCRIPTION OF THE INVENTION

FIG. 1 shows a u.v. irradiation apparatus 1 comprising a vessel in the form of a generally cylindrical bag 2 of silicone rubber mounted on support rollers 3 at least one of which is driven for rolling of the bag 2. The bag 2 has corrugated side wall means 4, the corrugations 5 extending longitudinally parallel to the central rotational axis 6 of the bag 2. Several u.v. radiation lamps 7 are disposed above and around the bag 2 parallel to its longitudinal axis 6 for irradiation of a blood product fluid 8 contained in the bag 2 and in particular as a thin film 9 thereof is carried up around the interior side 10 of the side wall mean 4 emerging from the main body 11 of the fluid 8, with corrugated side walls there is obtained a much larger effective irradiation zone with a conventional cylindrical vessel due to a shallow penetration of u.v. irradiation in blood and like fluids, thereby allowing substantially reduced processing times for sterilisation.

In order to maintain a substantially cylindrical form of the bag 2 there are desirably provided rigidifying means such as axially spaced rings 12 and/or transversely extending flanges 13 in between opposed corrugation side walls 14.

A second form of bag is shown in FIG. 2 in which like parts corresponding to those of FIG. 1 are indicated by like reference numbers. In this case the corrugations 15 extend annularly thereby helping to maintain a generally cylindrical form of the bag 2 without the need for addition rigidifying of the bottle and also allowing axial compression or expansion of the bag and hence variation of its internal volume. In this bottle the corrugations have a pitch of about 10 mm. the overall length and outside diameter of the bottle begin some 260 mm. and 50 mm., and the side wall means having a thickness in the range of 0.6 to 0.8 mm.

FIGS. 3 and 4, in which like parts corresponding to those in FIGS. 1 and 2 have been indicated by like reference numbers, show alternative embodiments in which the vessel 16 is in the form of a thin-walled plain tubular bag 17 of silicone rubber, provided with wall support means 18 comprising a u.v.—transparent cylindrical glass tube 19 in the embodiment of FIG. 3 and a cylindrical wire mesh cage 20 in the embodiment of FIG. 4. By this means the bag 17 can readily be rolled during an u.v.—irradiation phase whilst being fully collapsible before introduction of biological fluid 8 thereinto.

FIG. 5 shows a vessel in the form of a screw top semi-rigid bottle 21 of Teflon PFA (perfluoroalkoxy) of 500 or 1,000 ml capacity with a wall thickness of approximately 1.5 to 2 mm. which is commercially available from Azlon Products Ltd. of London, England.

The bottle 21 is simply supported on two rollers 3, one of which 22 is drivingly engaged with an electric drive motor 23. The U.V. lamps 7 in this case are provided with reflectors 24 to maximize efficiency by concentrating radiation on the fluid 6.

The motor 23 and lamps 7 are connected to a timer and control unit 25 formed and arranged for controlling the duration of the irradiation. Advantageously the apparatus includes circuit means (not shown) for detecting and indicating lamp failure to alert the operator to the danger of incomplete irradiation should one or more lamps fail during processing.

FIG. 6 shows a generally cylindrical vessel 26 supported on a turntable 27 provided with a rotary drive 28 for rotating the vessel 26 about a generally vertical axis. A suitable UV radiation source in the form of a plurality of UVA light tubes 29 (only one shown) is disposed generally parallel to and around the vessel 26.

EXAMPLE 1

Treatment of Human Blood

Venous blood (250 ml) is collected from a healthy young adult into bottle (250 ml. or 500 ml. size) made of silicone rubber (Dunlop Precision Rubbers Limited of Loughborough, England, having a shape shown in FIG. 1, and containing 2,000 units of preservative-free heparin (Weddell Pharmaceuticals Ltd., London, U.K.) or other anticoagulant e.g. CPDA.

The bottle is rolled at from 10 to 250 e.g. 140 rpm for from 5 to 30 e.g. 15 minutes under several u.v.—emitting florescent tubes extending parallel to the bottle. The irradiation chamber is air cooled with a fan.

Sterilisation of the blood is monitored by one or more of the following procedures:

(a) Separation of lymphocytes, culture and subsequent dosage with tritiated thymidine and subsequent liquid scintillation counting.

(b) Separation of lumphotcytes, culture and examination by electron microscope (c) Separation of lymphocytes and observation of response to tissue stains.

(d) Culture of bacteria by standard laboratory methods.

(e) Growth of viruses by standard laboratory methods.

(f) Study of Protozoans by light and electron microscopy and by in vivo passage in an animal species.

(g) Study of biological behaviour of Blood Platelets by standard in vitro haematological techniques, e.g. behaviour in an aggregometer and after exposure to collagen, ATP etc.

EXAMPLE 1

Inactivation of Bacteria in Fluid Samples

Using the apparatus of FIG. 1 the inactivation of bacteria using the apparatus and procedures of Example 1 was monitored as follows: Bacteria either Gram+ve (*Staph. albus*) or Gram-ve (*E. coli*) or spore-forming (*B. subtilis*) were added in concentrations $10^9$ per ml to whole blood or fluid media and submitted to rotation/-spinning in the UV radiation field and samples at 5 min. intervals were shown to be killed progessively so that by 20 min. or so the blood/,medium can be shown to be sterile by normal microbiological means. Contamination in systems envisaged to be treated would in practice never approach a concentration of bacteria as high as $10^9$ cells $ml^{-1}$

We claim:

1. An apparatus (1) suitable for sterilizing a biological fluid using ultra-violet irradiation, said apparatus comprising a vessel (2) for containing a biological fluid; said vessel (2) having side wall means (4) substantially transparent to ultra-violet radiation of an effective sterilizing wave length; a turning vessel support means (3) formed and arranged for supporting said vessel (2) and allowing said vessel (2) to turn on said support means (3); a drive means (23) formed and arranged for turning said vessel (2) on said support means (3); and an ultra-violet irradiation means (7) formed and arranged for irradiation at least part of said vessel (2) while it is turning on said support means (3), with ultra-violet radiation of said effective wavelength, whereby a thin layer (9) of said fluid (8) adjacent a surface (10) of said side wall means (4) is carried round past the ultra-violet irradiation means (7) and sterilized thereby and mixed with remaining fluid.

2. The apparatus according to claim 1 wherein said vessel (2) is generally tubular.

3. The apparatus according to claim 2 wherein said vessel support means (3) is formed and arranged for rolling of said vessel (2).

4. The apparatus according to claim 1 wherein said irradiation means (7) produces ultra-violet radiation in a wavelength range from 100 to 400 nm.

5. The apparatus according to claim 1 wherein said side wall means (4) is formed of an ultra-violet transparent material selected from the group consisting of: ultra-violet transparent glass, silicone, cellulose, and plastic materials.

6. The apparatus according to claim 5 wherein said plastic materials are selected from the group consisting of: polytetrafluoroethylene, fluorinatedethenepropene, low density polyethylene, and polyvinylchloride.

7. The apparatus according to claim 1 wherein the side wall means are corrugated side wall means.

8. The apparatus according to claim 1 wherein said vessel has flexible side wall means (4) formed and arranged so that said vessel is substantially collapsible when empty.

9. The apparatus (1) according to claim 3 wherein said vessel comprises a generally tubular bag (3) having side wall means (4) substantially transparent to said ultra-violet radiation.

10. The apparatus according to claim 9 further comprising side wall support means formed integrally with the side wall means (4) and including corrugations (15) formed in the side wall means (4) which extend circumferentially, axially, and obliquely with respect to a central rotational axis of the vessel (2).

11. A method of inactivating undesired micro-organisms in a biological fluid, comprising the steps of:
providing a vessel having side wall means substantially transparent to ultra-violet radiation of an effective inactivating wavelength for containing said fluid;
providing support means for rotatably supporting said vessel, and associated drive means for rotating said vessel on said support means;
placing said fluid in said vessel;
providing an ultra-violet irradiation means for supplying ultra-violet radiation of an effective sterilizing wavelength;
supporting said vessel on said supporting means and operating said associated drive means to rotate said vessel; and
exposing said rotating vessel and fluid to said irradiation for a period of time sufficient to substantially inactivate said undesired micro-organisms therein.

* * * * *